(12) United States Patent
Stumpf et al.

(10) Patent No.: US 6,280,737 B1
(45) Date of Patent: *Aug. 28, 2001

(54) HARPAGOSIDE-ENRICHED EXTRACT FROM HARPAGOPHYTUM PROCUMBENS AND PROCESSES FOR PRODUCING SAME

(75) Inventors: Karl-Heinz Stumpf; Hermann Jaggy, both of Karlsruhe; Rainer Oschmann, Landau; Egon Koch, Karlsruhe; Thomas Simmet, Bochum, all of (DE)

(73) Assignee: Dr. Willmar Schwabe GmbH & Co., Karlsruhe (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,043

(22) PCT Filed: Mar. 21, 1997

(86) PCT No.: PCT/DE97/00591

§ 371 Date: Feb. 22, 1999

§ 102(e) Date: Feb. 22, 1999

(87) PCT Pub. No.: WO97/34565

PCT Pub. Date: Sep. 25, 1997

(30) Foreign Application Priority Data

Mar. 21, 1996 (DE) .............................. 196 11 221
Dec. 10, 1996 (DE) .............................. 196 51 290

(51) Int. Cl.[7] ................................................. A01N 65/00
(52) U.S. Cl. ...................................................... 424/195.1
(58) Field of Search .......................................... 424/195.1

(56) References Cited

FOREIGN PATENT DOCUMENTS

| 2031386 | 12/1990 | (CA) . |
| 3940092 | 6/1991 | (DE) . |
| 0 524 873 A1 | 1/1993 | (EP) . |
| 2614791 | 11/1988 | (FR) . |

OTHER PUBLICATIONS

English Translation of Purchase Order No. 211138, Jan. 12, 1995.
English Translation of Invoice from Salus–Haus for Purchase Order No. 211138, Nov. 12, 1995.
English Translation of Client Information regarding purchases by Salus–Haus, Oct. 12, 1992.
English Translation of Specification of the Salus–Haus product 13RT183, Nov. 1995.
English Translation of Declaration of Dr. Ernst Schneider, Mar. 15, 2000.
Chrubasik et al., (1996) *Forsch Komplementarmed*, vol. 3, pp. 57–63.
Purchase order no. 211138, Jan. 12, 1995.
Invoice from Salus–Haus for Purchase order No. 211138, Nov. 12, 1995.
Client Information Regarding purchases by Salus–Haus, Oct. 12, 1992.
Specification of the Salus–Haus product 13RT183, Nov. 1995.
Declaration of Dr. Ernst Schneider, Mar. 15, 2000.
Caprasse, M., *J. Pharm. Belg.*, 35, 2, 143–149(1980).
Mousard et al., *Chemical Abstracts*, 117, p. 34, Abstract No. 117:163533z (1992).
Erdos et al., *Planta Medica*, 34, 97–108, (1978).
Database WPI, Derwent Publications Ltd., Abstract of KR9205686, (Jul. 1992).

*Primary Examiner*—Herbert J. Lilling
(74) *Attorney, Agent, or Firm*—McDonnell Boehnen Hulbert & Berghoff

(57) ABSTRACT

The disclosure relates to extracts from Harpagophytum procumbens with a high harpagoside content, to processes for producing them, such extracts containing no components capable of stimulating the synthesis of thromboxane $B_2$ and cysteinylleucotrienes, and to pharmaceutical compositions containing such extracts.

9 Claims, No Drawings

HARPAGOSIDE-ENRICHED EXTRACT FROM HARPAGOPHYTUM PROCUMBENS AND PROCESSES FOR PRODUCING SAME

This application is a 371 of PCT/DE97/00591 filed Mar. 21, 1997.

Due to many years of experience, tea preparations or extracts, respectively, from roots of devil's claw (radix harpagophyti) have been employed in the case of dyspeptic conditions as well as in the treatment of rheumatoid diseases (Sticher, O., DAZ 117 (1977), 1279–1284). The drug is composed of the underground parts and mainly of the secondary storage roots of Harpagophytum procumbens (Volk, O.H., DAZ 104 (1964), 573–576; F.C. Czygan, Zeitschrift fur Phytotherapie 8 (1987), 17–20).

M. Caprasse, J. Pharm. Belg., 1980, 35, 2, 143–149, reviews Harpagophytum procumbens and its properties. The finely pulverized root was extracted with methanol, the resulting extract was evaporated, the residue added with water, and the resulting aqueous solution was extracted 3 times with a 4:1 mixture of methylene chloride and n-butanol.

R.E. Moati, FR-A-2 614 791, describes a composition of 400 mg of Harpagophytum procumbens, 20 mg of selenium and 25 mg of zinc for the treatment of rheumatism and inflammations.

The commission E of the former Bundesgesundheitsamt took the reports and clinical observations into account by publishing a positive monography "Radix harpagophyti" in 1989. According to this publication, preparations from devil's claw roots are employed in the case of dyspeptic conditions (daily dose of 1.5 g of the drug) and in the supportive therapy of degenerative diseases of the motoric system (daily dose of 4.5 g of the drug) (Bundesanzeiger No. 43 of 02/03/1989). To date it has not been possible to attribute the efficacy to particular ingredients.

As the essential ingredients of the extracts there have been mentioned iridoid glycosides, in particular harpagoside, and also harpagide and procumbide. Furthermore, they contain high amounts of sugar (50–60%), fats, waxes, and sterines (Steinegger, Hänsel, Lehrbuch der Pharmakognosie und Phytopharmazie, Springer Verlag Berlin, Heidelberg, New York 1988, pp 608–610). Particularly, tea preparations (R. Jaspersen-Schib, DAZ 130 (1990), 71–73; F.-C. Czygan in M. Wichtl, Teedrogen WVA Stuttgart 1989, pp 495–497) as well as capsule and tablet preparations for oral administration containing simple aqueous or aqueous alcoholic extracts (Chrubasik et al., Forsch. Komplementarmed. 1996:3:57–63) are commercially available.

Recently, an antirheumatic effectivity has been shown in a clinical double-blind study. For this purpose, extracts have been employed ensuring a dosage of 50 mg of harpagoside per day (S. Chrubasik, R. Ziegler in Phytopharmaka 2—Forschung und klinische Anwendung—Loew, Rietbrock, eds., Steinkopf Verlag Danrstadt 1996 (pp 101–114)).

The conventional pharmaceutical preparations containing simple extracts show harpagoside contents of 1 to 3% (Chrubasik et al., Forsch. Komplementärmed. 1996:3:6–11) so that as high amounts of extract as 1500 to 4500 mg would be necessary to ensure an administration of 50 mg harpagoside/day. This again would require large drug formulations or a frequent or repeated intake of the preparation thereby leading to a decrease in patient compliance.

The object of the present invention is to provide novel extracts enriched in harpagoside content in which ingredients without or with undesired pharmacological effects have been depleted. It is a further object of the invention to provide methods for the preparation of such extracts as well as drug formulations containing those extracts.

The invention is based on the surprising finding that aqueous or aqueous alcoholic primary extracts generally having a harpagoside content of only 1 to 3% may be strongly enriched in harpagoside according to the invention by stirring with neat aliphatic alcohol or aliphatic keton or mixtures thereof up to values of at least 5% while ingredients having a stimulatory effect on the synthesis of thromboxane $B_2$ and cysteinyl-leucotrienes are reduced or eliminated.

The term "aqueous alcoholic primary extracts" refers to extracts obtained by extracting radix harpagophyti with a mixture of water and ethanol. The aliphatic alcohols contain from 1 to 4 C atoms, the aliphatic ketons contain from 3 to 4 C atoms. Preferably, for stirring there are used methanol, ethanol, propanol, isopropanol, n-butanol, isobutanol, tert butanol, aceton, butanon and the mixtures thereof. Ethanol is especially preferred. The stirring is performed at a temperature in the range of about 5 to 25° C. The term "stirring" refers to intimate mixing by stirring.

In a preferred embodiment the ground drug is extracted with 20% ethanol/water. Subsequently a concentration step is carried out, and the resulting primary extract is stirred with ethanol 96% at room temperature. The soluble fraction is separated from the insoluble fraction and dried. It contains at least 5% of harpagoside.

In a preferred embodiment the ground drug is extracted with 20% ethanol/water. Subsequently a concentration step is carried out, and the resulting primary extract is stirred with ethanol 96% at room temperature. The soluble fraction is separated from the insoluble fraction and dried. It contains at least 5% of harpagoside.

A further surprising finding was that extracts prepared according to the method described have a higher pharmacological activity in comparison to primary extracts but also to pure harpagoside. Conventional primary extracts have been found to contain ingredients leading to a potent stimulation of the synthesis of pro-inflammatory lipid mediators and thereby counteracting the desired antiphlogistic effects. These ingredients are depleted in the extracts of the invention. The depletion or removal, respectively, of these undesired ingredients is performed by the stirring according to the invention of the primary extract with the alcohol or keton or the mixtures thereof.

The extracts according to the invention may be used to prepare orally applicable solid or liquid drug preparations having an antirheumatic and antiphlogistic activity by adding conventional pharmaceutical adjuvants in a known manner.

The invention will be further illustrated with respect to the following Examples:

EXAMPLE 1

30 kg of dry secondary storage roots of Harpagophytum procumbens crushed by grinding were added with 300 kg of completely demineralized water heated to 85° C. and stirred for two hours. The extract was filtered under pressure via a plate filter. The plant material was again extracted with 120 kg of hot water at 85° C. for two hours, and the extract was filtered. The extracts from the two extraction stages were combined: 348 kg. Afterwards, the obtained extract was concentrated in a rotary evaporator under vacuum to 19 kg with a dry residue of 60.5%. The resulting thick extract was dried at a max. of 60° C. and a pressure of 20 mbar. This step gave 11.4 kg of dry extract having a harpagoside content of 2.25% (as determined by HPLC).

EXAMPLE 2

90 kg of dry secondary storage roots of flarpagopliytum procumbens were extracted in three batches with hot water according to Example 1. The combined extract solutions (1032 kg) were concentrated in a rotary evaporator under vacuum at 180–220 mbar and 50° C. to 67 kg with a dry residue of 51.2%. This concentrate, i.e. the primary extract, was added dropwise under stirring to 350 kg of ethanol 95% by weight at 20° C. (room temperature). For deposition of the precipitate formed the mixture was left for two hours without agitation. The supernatant was withdrawn and concentrated in a rotary evaporator to a dry residue of 54.4%. This concentrate was dried in a vacuum drying chamber at a maximum of 60° C. and a pressure of 20 mbar affording 7.56 kg of a harpagoside-rich dry extract having a harpagoside content of 7.3% (as determined by HPLC).

EXAMPLE 3

101.5 kg of dry secondary storage roots of Harpagophytum procumbens crushed via a 7 mm sieve were heated to 75° C. with 1420 kg of ethanol 20% by weight for two hours under stirring. After cooling to 50° C., the residue was filtered and again extracted with 1010 kg of ethanol 20% by weight at 75° C. The combined extract solutions were concentrated in a rotary evaporator under vacuum at 180–220 mbar/50° C. to 87 kg with a dry residue of 68%. This concentrate (primary extract) was added under stirring to 240 kg of ethanol 95% by weight. After the precipitate had deposited the supernatant was separated and concentrated in a rotary evaporator under vacuum at 250 mbar to 16 kg. This concentrate was dried in a vacuum drying chamber at a maximum of 65° C. and a pressure of 20 mbar affording 8.5 kg of a harpagoside-rich extract containing 12.7% of harpagoside (as determined by HPLC).

EXAMPLE 4

The precipitate obtained by stirring with ethanol according to Example 3 was dried in a vacuum drying chamber at 65° C. and a pressure of 20 mbar affording 21 kg of an extract fraction containing 0.35% harpagoside.

EXAMPLE 5

1.5 kg of ground dried secondary storage roots of Harpagophytum procumbens were extracted with 15 kg of ethanol 80% by weight for one hour at 60° C. After cooling, the extract solution was withdrawn via a filter layer. The extract residue was re-extracted with 15 kg of ethanol 80% by weight for one hour at 60° C. The combined extract solutions were concentrated at the rotary evaporator with a bath temperature of 50–60° C. under a vacuum of 120 mbar until no more ethanol distilled over. The concentrate was diluted to a dry residue of 10% by addition of completely demineralized water. This solution (primary extract) was intimately agitated three times each with 1800 g of n-butanol at room temperature. In each case the butanol phase formed (upper phase) was separated. At the rotary evaporator the combined butanol phases were concentrated to dryness under vacuum at 20–30 mbar. The dry extract was ground and redried in a vacuum drying chamber at 60° C. and 10 mbar affording 61 g of harpagoside-rich extract having a harpagoside content of 19.3% (as determined by HPLC).

EXAMPLE 6

Coated Tablet Containiiig the Extract According to the Invention

Coated tablets containing 200 or 400 mg, respectively, of the dry extract of the invention have the following composition:

| | | |
|---|---|---|
| Devil's claw dry extract according to Example 5 | 200 mg | 400 mg |
| Highly dispersed silicon dioxide | 5 mg | 10 mg |
| Polyvinyl pyrrolidone (mol. wt. of 25,000) | 3 mg | 6 mg |
| Crosslinked polyvinyl pyrrolidone | 5 mg | 10 mg |
| Magnesium stearate | 2 mg | 4 mg |
| Microcristalline cellulose | 35 mg | 70 mg |

The components were mixed and compressed to form tablets. The tablets were coated by a film coating on the basis of methyl hydroxypropyl cellulose.

Pharmacological Activity of Various Extracts

The pharmacological effects on the formation of pro-inflammatory lipid mediators were examined in whole human blood after stimulation with the calcium ionophor A23187 (10 mM, 60 min at 37° C.) according to the method of I. Weide, K. Tschorn, T. Simmet (Thrombosis Research 67, pp 123–134 (1992)). In this model for example glucocorticoids show an inhibitory action. The concentrations of cysteinyl-leucotrienes ($LTC_4$, $LTD_4$, and $LTE_4$) and of thromboxane $B_2$ were determined in plasma using a radio-immuno assay. Harpagoside or Harpagophytum extracts, respectively, proved to inhibit the biosynthesis of these substances in concentration-dependent manner. The results are summarized in Table I. It is clear from Table I that the inhibitory effect of the extracts according to the invention (prepared according to Example 2 or 3) on cysteinyl-LTs was more pronounced than that of the primary extract (prepared according to Example 1) or of pure harpagoside.

An examination of the precipitate which was removed from the primary extract according to Example 3 in order to enrich effective ingredients (Example 4) revealed that it has a clear stimulatory effect on the biosynthesis of cysteinyl-leucotrienes and $TXB_2$ (Table II) and therefore counteracts the desired anti-inflammatory effects.

TABLE I

Inhibition of the biosynthesis of cysteinyl-leucotrienes and $TXB_2$ in whole human blood after pre-incubation with harpagoside or Harpagophytum extracts (15 min at 37° C.) and subsequent stimulation with A23187 (10 mM, 37° C. for 60 min). The half-maximal inhibitory concentration ($IC_{50}$) based on the harpagoside content is shown.

| | $IC_{50}$ $TXB_2$ | $IC_{50}$ cysteinyl-LTs |
|---|---|---|
| Harpagoside | 48.6 mM | 39 mM |
| Harpagophytum extract (primary extract prepared according to Example 1) | >100 mM | 61.7 mM |
| Harpagoside-rich extract according to the invention (prepared according to Example 2) | 55.3 mM | 9.2 mM |

TABLE II

Stimulation of the biosynthesis of cysteinyl-leucotrienes and $TXB_2$ in whole human blood after pre-treatment with the extract fraction obtained according to Example 4 (15 min at 37° C.) and subsequent stimulation with A23187 (10 mM, 37° C. for 60 min). The percentage of stimulation in comparison to a control sample at a concentration of 1 mg/ml is shown.

| | $IC_{50}$ $TXB_2$ | $IC_{50}$ cysteinyl-LTs |
|---|---|---|
| Harpagophytum extract fraction of Example 4 | +28.7% | +70.5% |

The methods for analysis of thromboxane $B_2$ and cysteinyl-leucotrienes are detailed in the following references:

Simmet Th., Luck W. (1989), Clotting of whole human blood induces cysteinyl-leucotriene formation. *Thromb Res* 54:423–433.

Simmet Th., Weide I. (1991), Thromboxane and cysteinyl-leucotriene formation are differentially activated in spontaneously clotting whole human blood in vitro. *Thromb Res* 62:249–261.

Weide I., Tschorn K., Simmet Th. (1992), EfTects of cyclooxygenase inhibitors on ex vivo cysteinyl-leucotriene production by whole human blood allowed to clot spontaneously. Comparison to stimulated blood. *Thromb Res* 67:123–134.

Weide I., Simmet Th. (1993), Leucotriene formation by peripheral monocytes in contact-activated human blood, *Thromb Res* 71:185–192.

Weide I., Romisch J., Simmet Th. (1994), Contact activation triggers stimulation of the monocyte 5-lipoxygenase pathway via plasmin. *Blood* 83:1941–1951.

What is claimed is:

1. A drug extract from Harpagophytum procumbens obtainable by the steps of:
    a) extracting the drug from Harpagophytum procumbens with water or a mixture of ethanol and water,
    b) concentrating the resulting extract;
    c) stirring the concentrate obtained at temperatures of 5 to 25° C. with a neat aliphatic alcohol having 1–4 carbon atoms or an aliphatic ketone having 3 to 4 carbon atoms or the mixtures thereof; and
    d) separating the insoluble fraction from the obtained soluble fraction, wherein the soluble fraction is the drug extract and has a strongly reduced content in ingredients having stimulatory effects on the synthesis of thromboxane $B_2$ and cysteinyl-leucotrienes.

2. The extract according to claim 1 which is obtained by the additional step of drying the resulting soluble fraction.

3. The extract according to claim 2 having a content of at least 5% harpagoside.

4. A process for the preparation of the drug extract from Harpagophytum procumbens according to claim 1, comprising:
    a) extracting the drug with water or a mixture of ethanol and water;
    b) concentrating the resulting extract;
    c) stirring the concentrate obtained at temperatures of 5 to 25° C. with a neat aliphatic alcohol having 1–4 carbon atoms or an aliphatic ketone having 3 to 4 carbon atoms or the mixtures thereof; and
    d) separating the insoluble fraction from the obtained soluble fraction, wherein the soluble fraction is the drug extract and has a strongly reduced content in ingredients having stimulatory effects on the synthesis of thromboxane $B_2$ and cysteinyl-leucotrienes.

5. The process according to claim 4 wherein for stirring there is used methanol, 96% ethanol, propanol, isopropanol, butanol, butanone, acetone, or a mixture thereof.

6. A process according to claim 4 further comprising drying the resulting soluble fraction.

7. A pharmaceutical composition containing an extract according to any of claims 1 to 3.

8. A method of treating a human suffering from rhematoid arthritis, the method comprising administering an effective antirheumactic amount of a compound according to any one of claims 1–3 to a patient in need thereof.

9. A method of treating a human suffering from inflammation and/or fever, the method comprising administering an effective antiphlogistic amount of a compound according to any one claims 1–3 to a patient in need thereof.

* * * * *